US005512549A

United States Patent [19]

Chen et al.

[11] Patent Number: 5,512,549
[45] Date of Patent: Apr. 30, 1996

[54] GLUCAGON-LIKE INSULINOTROPIC PEPTIDE ANALOGS, COMPOSITIONS, AND METHODS OF USE

[75] Inventors: Victor J. Chen, Indianapolis; Richard D. DiMarchi, Carmel; David L. Smiley, Greenfield; Russell D. Stucky; Aidas V. Kriauciunas, Indianapolis, all of Ind.

[73] Assignee: Eli Lilly and Company, Indianapolis, Ind.

[21] Appl. No.: 324,960

[22] Filed: Oct. 18, 1994

[51] Int. Cl.$^6$ .......................... A61K 38/00; A61K 38/26; C07K 14/605
[52] U.S. Cl. ............................. 514/12; 530/308; 530/324
[58] Field of Search ................................. 530/308, 324; 514/12

[56] References Cited

U.S. PATENT DOCUMENTS

| | | | |
|---|---|---|---|
| 5,070,188 | 12/1991 | Njieha et al. | 530/324 |
| 5,118,666 | 6/1992 | Habener | 514/12 |
| 5,120,712 | 6/1992 | Habener | 514/12 |

FOREIGN PATENT DOCUMENTS

| | | |
|---|---|---|
| 0082731 | 12/1982 | European Pat. Off. |
| 0619322A2 | 2/1994 | European Pat. Off. |
| WO87/06941 | 11/1987 | WIPO |
| WO90/11296 | 10/1990 | WIPO |
| WO91/11457 | 8/1991 | WIPO |
| WO93/18786 | 9/1993 | WIPO |
| WO93/25579 | 12/1993 | WIPO |

OTHER PUBLICATIONS

Ser. No. 08/164,277, Galloway, et al, filing date Dec. 9, 1993.
Kreymann, et. al., "Glucagon-Like Peptide 7–36 A Physiological Incretin In Man", *The Lancet*, vol. 2, pp. 1300–1303 (Dec. 5, 1987).
Holst, et. al., "Truncated glucagon–like peptide I, an insulin-releasing hormone from the distal gut", *FEBS Letters*, vol. 211, No. 2, pp. 169–174 (Jan. 1987).
Mojsov, et. al., "Insulinotropic: Glucagon–like Peptide I (7–37) Co.–encoded in the Glucagon Gene Is a Potent Stimulator of Insulin Release in the Perfused Rat Pancreas", *The American Society for Clinical Investigation, Inc.*, vol. 79, pp. 616–619 (Feb. 1987).
Goke, et. al., "Glucagon like peptide–1 (7–36) amide is a new incretin/enterogastrone candidate", *European Journal of Clinical Investigation*, vol. 21, pp. 135–144 (1991).
Suzuki, et. al., "Effects Of GLP–1 And Its Fragment Peptides On Pancreatic Hormone Release", *Diabetes Research and Clinical Practice*, Supp. 1, vol. 5, ORA–007–007, p. S30 (1988).
Weir, et. al., "Glucagonlike Peptide I (7–37) Actions on Endocrine Pancreas", *Diabetes*, vol. 38, pp. 338–342 (Mar. 1989).
Komatsu, et. al., "Glucagonostatic and Insulinotropic Action of Glucagonlike Peptide I–(7–36)–Amide", *Diabetes*, vol. 38, pp. 903–905, (Jul. 1989).
Orskov, et. al., "Complete Sequences of Glucagon–like Peptide–1 from Human and Pig Small Intestine", *The Journal of Biological Chemistry*, vol. 264, No. 22, pp. 12826–12929, (Aug. 5, 1989).
Takahashi, et. al., "Radioimmunoassay For Glucagon–Like Peptide-1 In Human Plasma Using N–Terminal And C–Terminal Directed Antibodies: A Physiologic Insulinotropic Role of GLP–1 (7–36 Amide)", *Biomedical Research* vol. 11 (2), pp. 99–108, (1990).
Mojsov, "Structural requirements for biological activity of glucagon–like peptide–I", *Int J Peptide Protein Res*, vol. 40, pp. 333–343 (1992).
Orskov, "Glucagon–like peptide–1, a new hormone of the entero–insular axis", *Diabetologia*, vol. 35, pp. 701–711 (1992).
Thorens, et. al., "Glucagon–Like Peptide–I and the Control of Insulin Secretion in the Normal State and in NIDDM", *Diabetes*, vol. 42, pp. 1219–1225 (Sep. 1992).
Nauck, et. al., "Normalization of fasting hyperglycaemia by exogenous glucagon–like peptide 1 (7–36 amide in Type 2 (non–insulin–dependent) diabetic patients", *Diabetologia*, vol. 36, pp. 741–744 (1993).
Nauck, et. al., "Preserved Incretin Activity of Glucagon–like Peptide 1 (7–36 Amide) but Not of Synthetic Human Gastric Inhibitory Polypeptide in Patients with Type–2 Diabetes Mellitus", *The American Society for Clinical Investigation, Inc.*, vol. 91, pp. 301–307, (Jan. 1993).
Hvidberg, et al., "Effect of Glucagon-like Peptide–1 (proglucagon 78–107 amide) on Hepatic Glucose Production in Healthy Man", *Metabolism*, vol. 43, No. 1, pp. 104–108, (Jan. 1994).
Fehmann, et al, "Insulinotropic Glucagonlike Peptide–I (7–37) (7–36) Amide A New Incretin Hormone", *TEM*, vol. 3, No. 5, 158–163, (1992).
Hashimoto, et al, "Synthesis of Palmitoyl Derivatives of Insulin and Their Biological Activities", *Pharmaceutical Research*, vol. 6, No. 2, 171–176 (1989).
Suzuki, S., et al. "Comparison of the Effects of Various C–Terminal and N–Terminal Fragment Peptides of Glucagon–Like Peptide–1 on Insulin and Glucagon Release from the Isolated Perfused Rat Pancreas" *Endocrinology*, vol. 125, No. 6, 3109–3114 (1989).

*Primary Examiner*—Jill Warden
*Assistant Examiner*—Benet Prickril
*Attorney, Agent, or Firm*—Ronald S. Maciak; David E. Boone

[57] ABSTRACT

Glucagon-like insulinotropic peptide (GLP-1(7-37)) analogs and derivatives are disclosed. The analogs include amino acid substitutions, amino and carboxyl terminal modifications, and $C_6$–$C_{10}$ acylations. The claimed compounds stimulate the secretion or biosynthesis of insulin in poorly functioning beta cells and are therefore useful in treating Type II diabetics

28 Claims, No Drawings

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
    ( A ) LENGTH: 29 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Protein
    ( B ) LOCATION:
    ( D ) OTHER INFORMATION: /label=N- terminal modifications
      / note ="organic moeity"

( i x ) FEATURE:
    ( A ) NAME/KEY: Protein
    ( B ) LOCATION: 19
    ( D ) OTHER INFORMATION: /label=substitution
      / note="Xaa-Lysine or Arginine"

( i x ) FEATURE:
    ( A ) NAME/KEY: Protein
    ( B ) LOCATION: 27
    ( D ) OTHER INFORMATION: /label=acylation
      / note="Epsilon amino group is C6-C10 acylated"

( i x ) FEATURE:
    ( A ) NAME/KEY: Protein
    ( B ) LOCATION: 29
    ( D ) OTHER INFORMATION: /label=C- terminus
      / note="C-terminus is OH or glycine-OH"

( x i ) SEQUENCE DESCRIPTION: SEQ ID NO:1:

Ala Glu Gly Thr Phe Thr Ser Asp Val Ser Ser Tyr Leu Glu Gly Gln
 1           5                   10                  15

Ala Ala Xaa Glu Phe Ile Ala Trp Leu Val Lys Gly Arg
            20                  25

GLUCAGON-LIKE INSULINOTROPIC PEPTIDE ANALOGS, COMPOSITIONS, AND METHODS OF USE

FIELD OF INVENTION

The present invention relates to organic and peptide chemistry as applied to pharmaceutical research and development. The invention provides novel peptide derivatives and compositions that are useful for up-regulating insulin expression in mammals and for treating diabetes.

BACKGROUND OF THE INVENTION

Endocrine secretions of pancreatic islets are regulated by complex control mechanisms driven not only by blood-borne metabolites such as glucose, amino acids, and catecholamines, but also by local paracrine influences. The major pancreatic islet hormones, glucagon, insulin and somatostatin, interact with specific pancreatic cell types (A, B, and D cells, respectively) to modulate the secretory response. Although insulin secretion is predominantly controlled by blood glucose levels, somatostatin inhibits glucose-mediated insulin secretion. In addition to inter-islet paracrine regulation of insulin secretion, there is evidence to support the existence of insulinotropic factors in the intestine. This concept originates from observations that glucose taken orally is a much more potent stimulant of insulin secretion than is a comparable amount of glucose given intravenously.

The human hormone glucagon is a 29-amino acid hormone produced in pancreatic A-cells. The hormone belongs to a multigene family of structurally related peptides that include secretin, gastric inhibitory peptide, vasoactive intestinal peptide and glicentin. These peptides variously regulate carbohydrate metabolism, gastrointestinal mobility and secretory processing. However, the principal recognized actions of pancreatic glucagon are to promote hepatic glycogenolysis and glyconeogenesis, resulting in an elevation of blood sugar levels. In this regard, the actions of glucagon are counter regulatory to those of insulin and may contribute to the hyperglycemia that accompanies Diabetes mellitus (Lund, P. K., et al., *Proc. Natl. Acad. Sci. U.S.A.*, 79:345–349 (1982)).

When glucagon binds to its receptor on insulin producing cells, cAMP production increases which in turn stimulates insulin expression (Korman, L. Y., et al., Diabetes, 34:717–722 (1985)). Moreover, high levels of insulin down-regulate glucagon synthesis by a feedback inhibition mechanism (Ganong, W. F., *Review of Medical Physiology*, Lange Publications, Los Altos, Calif., p. 273 (1979)). Thus, the expression of glucagon is carefully regulated by insulin, and ultimately by serum glucose levels.

Preproglucagon, the precursor form of glucagon, is encoded by a 360 base pair gene and is processed to form proglucagon (Lund, et al., *Proc. Natl. Acad. Sci. U.S.A.* 79:345–349 (1982)). Patzelt, et al. (Nature, 282:260–266 (1979)) demonstrated that proglucagon is further processed into glucagon and a second peptide. Later experiments demonstrated that proglucagon is cleaved carboxyl to Lys-Arg or Arg-Arg residues (Lund, P. K., et al., Lopez L. C., et al., *Proc. Natl. Acad. Sci. U.S.A.*, 80:5485–5489 (1983), and Bell, G. I., et al., *Nature* 302:716–718 (1983)). Bell, G. I., et al., also discovered that proglucagon contained three discrete and highly homologous peptide regions which were designated glucagon, glucagon-like peptide 1 (GLP-1), and glucagon-like peptide 2 (GLP-2). Lopez, et al., demonstrated that GLP-1 was a 37 amino acid peptide and that GLP-2 was a 34 amino acid peptide. Analogous studies on the structure of rat preproglucagon revealed a similar pattern of proteolytic cleavage at Lys-Arg or Arg-Arg residues, resulting in the formation of glucagon, GLP-1, and GLP-2 (Heinrich, G., et al., *Endocrinol.*, 115:2176–2181 (1984)). Finally, human, rat, bovine, and hamster sequences of GLP-1 have been found to be identical (Ghiglione, M., et al., *Diabetologia*, 27:599–600 (1984)).

The conclusion reached by Lopez, et al., regarding the size of GLP-1 was confirmed by studying the molecular forms of GLP-1 found in the human pancreas (Uttenthal, L. O., et al. *J. Clin. Endocrinol. Metabol.*, 61:472–479 (1985)). Their research showed that GLP-1 and GLP-2 are present in the pancreas as 37 and 34 amino acid peptides respectively.

The similarity between GLP-1 and glucagon suggested to early investigators that GLP-1 might have biological activity. Although some investigators found that GLP-1 could induce rat brain cells to synthesize cAMP (Hoosein, N. M., et al., *Febs Lett.* 178:83–86 (1984)), other investigators failed to identify any physiological role for GLP-1 (Lopez, L. C., et al. supra). The failure to identify any physiological role for GLP-1 caused some investigators to question whether GLP-1 was in fact a hormone and whether the relatedness between glucagon and GLP-1 might be artifactual.

It has now been shown that biologically processed forms of GLP-1 have insulinotropic properties and may delay gastric emptying. GLP-1(7–34) and GLP-1(7–35) are disclosed in U.S. Pat. No. 5,118,666, herein incorporated by reference. GLP-1(7–37) is disclosed in U.S. Pat. No: 5,120,712, herein incorporated by reference.

Variants and analogs of GLP-1 are known in the art. These variants and analogs include, for example, GLP-1(7–36), Gln$^9$-GLP-1(7–37), D-Gln$^9$-GLP-1(7–37), acetyl-Lys$^9$-GLP-1(7–37), Thr$^{16}$-Lys$^{18}$-GLP-1(7–37), and Lys$^{18}$-GLP-1(7–37). Derivatives of GLP-1 include, for example, acid addition salts, carboxylate salts, lower alkyl esters, and amides (see, e.g., WO91/11457). Generally, the various disclosed forms of GLP-1 are known to stimulate insulin secretion (insulinotropic action) and cAMP formation (see, e.g., Mojsov, S., *Int. J. Peptide Protein Research*, 40:333–343 (1992)).

More importantly, numerous investigators have demonstrated a predictable relationship between various in vitro laboratory experiments and mammalian, especially human, insulinotropic responses to exogenous administration of GLP-1, GLP-1(7–36) amide, and GLP-1(7–37) acid (see, e.g., Nauck, M. A., et al., *Diabetologia*, 36:741–744 (1993); Gutniak, M., et al., *New England J. of Medicine*, 326(20):1316–1322 (1992); Nauck, M. A., et al., *J. Clin. Invest.*, 91:301–307 (1993); and Thorens, B., et al., *Diabetes*, 42:1219–1225 (1993)).

The fundamental defects responsible for causing hyperglycemia in mature onset diabetes include impaired secretion of endogenous insulin and resistance to the effects of insulin by muscle and liver tissue (Galloway, J. S., *Diabetes Care*, 13:1209–1239, (1990)). The latter defect results in excess glucose production in the liver. Thus, whereas a normal individual releases glucose at the rate of approximately 2 mg/kg/minute, a patient with mature onset diabetes releases glucose at a rate exceeding 2.5 mg/kg/minute, resulting in a net excess of at least 70 grams of glucose per 24 hours.

Because there exists exceedingly high correlations between hepatic glucose production, fasting blood glucose levels, and overall metabolic control as indicated by glycohemoglobin measurements (Galloway, J. A., supra; and Galloway, J. A., et al., *Clin. Therap.*, 12:460–472 (1990)), it is readily apparent that control of fasting blood glucose is essential for achieving overall normalization of metabolism sufficient to prevent hyperglycemic complications. Since existing insulin therapies rarely normalize hepatic glucose production without producing significant hyperinsulinemia and hypoglycemia (Galloway, J. A., and Galloway, J. A., et al., supra) alternative approaches are needed. Thereapy based on administration of GLP-1 analogs is one such approach and is an object of the present invention.

Presently, therapy involving the use of GLP-1 type molecules has presented a significant problem because the serum half-life of such peptides is quite short. For example, GLP-1 (7–37) has a serum half-life of only 3 to 5 minutes. Presently, the activity of dipeptidyl-peptidase IV (DPP IV) is believed to readily inactivate GLP-1(7–37) in addition to rapid absorption and clearance following parenteral administration. Thus, there exists a critical need for biologically active GLP-1 (7–37) analogs that possess extended pharmacodynamic profiles following parenteral administration.

Accordingly, the primary object of this invention is to provide novel, chemically modified peptides that not only stimulate insulin secretion in type II diabetics but also produce other beneficial insulinotropic responses. The compounds of the present invention persist in the serum for longer periods than native GLP-1(7–37) either by showing resistance to DPP IV or by being absorbed and cleared slower than native GLP-1(7–37) following parenteral administration. Most surprisingly, some compounds of the present invention demonstrated a synergistic effect as individual alterations to GLP-1(7–37) failed to add-up to the biological performance of compounds that contained all of the alterations.

SUMMARY OF THE INVENTION

The present invention provides compounds of the general formula:

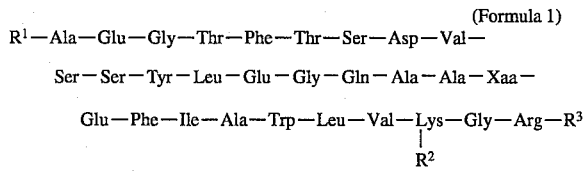

(Formula 1)

wherein $R^1$ is selected from the group consisting of 4-imidazopropionyl (des-amino-histidyl), 4-imidazoacetyl, or 4-imidazo-α, αdimethyl-acetyl;

$R^2$ is selected from the group consisting of $C_6$–$C_{10}$ unbranched acyl, or is absent;

$R^3$ is selected from the group consisting of Gly-OH or $NH_2$; and,

Xaa is Lys or Arg.

The present invention also provides pharmaceutical compositions comprising a compound of the present invention in combination with a pharmaceutically acceptable carrier, diluent, or excipient. The present invention further provides a method for treating non-insulin dependent diabetes mellitus in a mammal in need of such treatment comprising administering an effective amount of a compound of the present invention to said mammal.

DETAILED DESCRIPTION OF THE INVENTION

In one embodiment, the present invention provides analogs of naturally-occurring GLP-1(7–37) that arise from adding various R groups via a peptide bond to the amino terminus of the peptide portion of Formula 1. Optionally, further compounds of the invention are made by acylating the epsilon amino group of the $Lys^{34}$ residue and by making limited amino acid substitutions at position 26 or by altering the carboxy terminus. Therefore, preparing the polypeptide backbone of Formula 1 is a logical first step when preparing compounds of the present invention.

It should be noted that this specification uses the nomenclature scheme that has developed around processed forms of GLP-1. In this scheme, the amino terminus of the known GLP-1(7–37) OH has been assigned number 7 and the carboxy terminus number 37. Therefore, the first Ala residue of Formula 1 corresponds to residue 8 of GLP-1(7–37)OH. Likewise Xaa in Formula 1 corresponds to residue 26 of GLP-1(7–37)OH and so forth.

Given the sequence information herein disclosed and the state of the art in solid phase protein synthesis, the protein portion of Formula 1 can be prepared via chemical synthesis. Also, recombinant DNA techniques may be used to express the protein backbone of Formula 1.

The principles of solid phase chemical synthesis of polypeptides are well known in the art and may be found in general texts in the area such as Dugas, H. and Penney, C., *Biooraanic Chemistry* (1981) Springer-Verlag, New York, pgs. 54–92, Merrifield, J. M., *Chem. Soc.*, 85:2149 (1962), and Stewart and Young, *Solid Phase Peptide Synthesis*, pp. 24–66, Freeman (San Francisco, 1969).

For example, the protein portion of Formula 1 may be synthesized by solid-phase methodology utilizing a 430A peptide synthesizer (PE-Applied Biosystems, Inc., 850 Lincoln Center Drive, Foster City, Calif. 94404) and synthesis cycles supplied by PE-Applied Biosystems. Boc amino acids and other reagents are commercially available from PE-Applied Biosystems and other chemical supply houses. Sequential Boc chemistry using double couple protocols are applied to the starting p-methyl benzhydryl amine resins for the production of C-terminal carboxamides. For the production of C-terminal acids, the corresponding PAM resin is used. Asn, Gln, and Arg are coupled using preformed hydroxy benzotriazole esters. The following side chain protecting groups may be used:

Arg, Tosyl

Asp, cyclohexyl

Glu, cyclohexyl

Ser, Benzyl

Thr, Benzyl

Tyr, 4-bromo carbobenzoxy

Boc deprotection may be accomplished with trifluoroacetic acid in methylene chloride. Following completion of the synthesis the peptides may be deprotected and cleaved from the resin with anhydrous hydrogen fluoride (HF) containing 10% meta-cresol. Cleavage of the side chain protecting group(s) and of the peptide from the resin is carried out at −5° C. to 5° C., preferably on ice for 60 minutes. After removal of the HF, the peptide/resin is washed with ether, and the peptide extracted with glacial acetic acid and lyophilized.

The preparation of protected, unprotected, and partially protected GLP-1 molecules has been described in the art. See U.S. Pat. No. 5,120,712 and 5,118,666, herein incorporated by reference, and Orskov, C., et al., *J. Biol. Chem.*, 264(22):12826–12829 (1989) and WO 91/11457 (Buckley, D. I., et al., published Aug. 8, 1991).

Likewise, the state of the art in molecular biology provides the ordinarily skilled artisan another means by which the protein portion of Formula 1 can be obtained. Although it may be produced by solid phase peptide synthesis or recombinant methods, recombinant methods may be preferable because higher yields are possible. The basic steps in recombinant production are:

a) isolating a natural DNA sequence encoding GLP-1 or constructing a synthetic or semi-synthetic DNA coding sequence for GLP-1, b) placing the coding sequence into an expression vector in a manner suitable for expressing proteins either alone or as a fusion proteins, c) transforming an appropriate eukaryotic or prokaryotic host cell with the expression vector, d) culturing the transformed host cell under conditions that will permit expression of a GLP-1 intermediate, and e) recovering and purifying the recombinantly produced protein.

As previously stated, the coding sequences may be wholly synthetic or the result of modifications to the larger, native glucagon-encoding DNA. A DNA sequence that encodes preproglucagon is presented in Lund, et al., *Proc. Natl. Acad. Sci. U.S.A.* 79:345–349 (1982) and may be used as starting material in the semisynthetic production of the compounds of the present invention by altering the native sequence to achieve the desired results.

Synthetic genes, the in vitro or in vivo transcription and translation of which results in the production of the protein portion of Formula 1, may be constructed by techniques well known in the art. Owing to the natural degeneracy of the genetic code, the skilled artisan will recognize that a sizable yet definite number of DNA sequences may be constructed, all of which encode the polypeptide of Formula 1.

The methodology of synthetic gene construction is well known in the art. See Brown, et al. (1979) *Methods in Enzymology,* Academic Press, N.Y., Vol. 68, pgs. 109–151. DNA sequences that encode the protein backbone of Formula 1 can be designed based on the amino acid sequences herein disclosed. Once designed, the sequence itself may be generated using conventional DNA synthesizing apparatus such as the Model 380A or 380B DNA synthesizers (PE-Applied Biosystems, Inc., 850 Lincoln Center Drive, Foster City, Calif. 94404).

To effect expression of the polypeptide of Formula 1, one inserts the engineered synthetic DNA sequence in any one of many appropriate recombinant DNA expression vectors through the use of appropriate restriction endonucleases. See generally Maniatis et al. (1989) *Molecular Cloning; A Laboratory Manual,* Cold Springs Harbor Laboratory Press, N.Y., Vol. 1–3. Restriction endonuclease cleavage sites are engineered into either end of the GLP-1 intermediate-encoding DNA to facilitate isolation from, and integration into, known amplification and expression vectors. The particular endonucleases employed will be dictated by the restriction endonuclease cleavage pattern of the parent expression vector to be employed. The choice of restriction sites are chosen so as to properly orient the coding sequence with control sequences to achieve proper in-frame reading and expression of the protein of interest. The coding sequence must be positioned so as to be in proper reading frame with the promoter and ribosome binding site of the expression vector, both of which are functional in the host cell in which the protein is to be expressed.

To achieve efficient transcription of the synthetic gene, it must be operably associated with a promoter-operator region. Therefore, the promoter-operator region of the synthetic gene is placed in the same sequential orientation with respect to the ATG start codon of the synthetic gene.

A variety of expression vectors useful for transforming prokaryotic and eukaryotic cells are well known in the art. See *The Promega Biological Research Products Catalogue* (1992) (Promega Corp., 2800 Woods Hollow Road, Madison, Wis., 53711–5399); and *The Stratagene Cloning Systems Catalogue* (1992) (Stratagene Corp., 11011 North Torrey Pines Road, La Jolla, Calif., 92037). Also, U.S. Pat. No. 4,710,473 describes circular DNA plasmid transformation vectors useful for expression of exogenous genes in *E. coli* at high levels. These plasmids are useful as transformation vectors in recombinant DNA procedures and (a) confer on the plasmid the capacity for autonomous replication in a host cell;

(b) control autonomous plasmid replication in relation to the temperature at which host cell cultures are maintained;

(c) stabilize maintenance of the plasmid in host cell populations;

(d) direct synthesis of a protein prod. indicative of plasmid maintenance in a host cell population;

(e) provide in series restriction endonuclease recognition sites unique to the plasmid; and (f) terminate mRNA transcription.

These circular DNA plasmids are useful as vectors in recombinant DNA procedures for securing high levels of expression of exogenous genes.

Having constructed an expression vector for the protein of Formula 1, the next step is to place the vector into a suitable cell and thereby construct a recombinant host cell useful for expressing the polypeptide. Techniques for transforming cells with recombinant DNA vectors are well known in the art and may be found in such general references as Maniatis, et al. supra. Host cells made be constructed from either eukaryotic or prokaryotic cells.

Prokaryotic host cells generally produce the protein at higher rates and are easier to culture. Proteins which are expressed in high-level bacterial expression systems characteristically aggregate in granules or inclusion bodies which contain high levels of the overexpressed protein. Such protein aggregates typically must be solubilized, denatured and refolded using techniques well known in the art. See Kreuger, et al. (1990) in *Protein Folding,* Gierasch and King, eds., pgs 136–142, American Association for the Advancement of Science Publication No. 89-18S, Washington, D.C.; and U.S. Pat. No. 4,923,967.

Having preparing the polypeptide backbone of Formula 1, an imidazole, as defined above in the "Summary of the Invention," is added to the amino terminus to produce various embodiments of the present invention. Coupling the imidazolic group to the polypeptide of Formula 1 is accomplished by synthetic chemical means. Because all of the various organic groups contemplated in this invention contain a carboxylic acid, the imidazolic group can be added by solid phase protein synthesis analogous to adding an amino acid to the N-terminus of a polypeptide. Alternatively, an activated ester of the imidazolic group can be added by standard chemical reaction methods.

Preferred imidazolic groups of the present invention are:

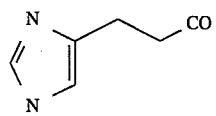

4-imidazopropionyl (des-amino-histidyl)
4-imidazoacetyl

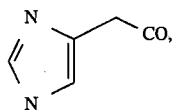

and
4-imidazo-α,αdimethyl-acetyl

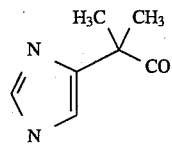

The most preferred group is 4-imidazopropionyl.

Further embodiments of the present invention are made by acylating the epsilon amino group of the $Lys^{34}$ residue. Straight chain acyl additions containing between 6 to 10 carbon atoms are preferred and unbranched $C_8$ is most preferred.

Other embodiment of the present invention include amino acid substitutions at position 26 (Xaa) of Formula 1. Lys, and Arg are acceptable at this position, though Arg is preferred.

Modifications at the carboxy terminus are also included in the present invention. As such $R^3$ may be Gly-OH or $NH_2$; Gly-OH is preferred over the carboxy terminal amide embodiments.

Addition of an acyl group to the epsilon amino group of $Lys^{34}$ may be accomplished using any one of a variety of methods known in the art. See *Bioconjugate Chem.* "Chemical Modifications of Proteins: History and Applications" pages 1, 2–12 (1990); Hashimoto et al., *Pharmacuetical Res.* "Synthesis of Palmitoyl Derivatives of Insulin and their Biological Activity" Vol. 6, No: 2 pp.171–176 (1989).

For example, the N-hydroxy-succinimide ester of octanoic acid can be added to the lysyl-epsilon amine using 50% acetonitrile in borate buffer. The peptide can be acylated either before or after the imidazolic group is added. Moreover, if the peptide is prepared recombinantly, acylation prior to enzymatic cleavage is possible.

The present invention also includes salt forms of GLP-1(7–37) analogs. Compounds of the invention may be sufficiently acidic or sufficiently basic to react with any of a number of inorganic bases, and inorganic and organic acids, to form a salt. Acids commonly employed to form acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesutfonate, propanesulfonate, naphthalene-1-sulfonate, naphthalene-2-sulfonate, mandelate, and the like. Preferred acid addition salts are those formed with mineral acids such as hydrochloric acid and hydrobromic acid, and, especially, hydrochloric acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, and the like. Salt forms of GLP-1(7–37) analogs are particularly preferred. When the compounds of the invention are used for therapeutic purposes, those compounds may also be in the form of a salt, but the salt must be pharmaceutically acceptable.

GLP-1(7–37) analogs of the present invention demonstrate insulinotropic activity. The term "insulinotropic activity" relates to the ability of a substance to stimulate, or cause the stimulation of, the synthesis or expression of the hormone insulin.

The insulinotropic property of a compound may be determined by providing that compound to animal cells, or injecting that compound into animals and monitoring the release of immunoreactive insulin (IRI) into the media or circulatory system of the animal, respectively. The presence of IRI is detected through the use of a radioimmunoassay which can specifically detect insulin.

Although any radioimmunoassay capable of detecting the presence of IRI may be employed, a modification of the assay may also be used. See J. D. M., et al., *Acta Endocrinol.*, 70:487–509 (1972). The insulinotropic property of a compound may also be determined by pancreatic infusion. See Penhos, J. C., et al., *Diabetes*, 18:733–738 (1969).

The present invention also provides pharmaceutical compositions comprising a compound of the present invention in combination with a pharmaceutically acceptable carrier, diluent, or excipient. Such pharmaceutical compositions are prepared in a manner well known in the pharmaceutical art, and are administered individually or in combination with other therapeutic agents, preferably via parenteral routes. An especially preferred route is by subcutaneous administration.

Parenteral dosages may range from about 1 pg/kg to about 1,000 μg/kg of body weight, although lower or higher dosages may be administered. The required dosage will depend upon the severity of the condition of the patient and upon such criteria as the patient's height, weight, sex, age, and medical history.

In making the compositions of the present invention, the active ingredient, which comprises at least one compound of the present invention, is usually mixed with an excipient or diluted by an excipient. When an excipient is used as a diluent, it may be a semi-solid or liquid material which acts as a vehicle, carrier, or medium for the active ingredient. Liquid excipients are preferred.

In preparing a formulation, it may be necessary to mill the active compound to provide the appropriate particle size prior to combining with the other ingredients. If the active compound is substantially insoluble, it ordinarily is milled to particle size of less than about 200 mesh. If the active compound is substantially water soluble, the particle size is normally adjusted by milling to provide a substantially uniform distribution in the formulation, e.g., about 40 mesh.

The compositions of the invention can be formulated so as to provide quick, sustained or delayed release of the active ingredient after administration to the patient by employing procedures well known in the art. The compositions are preferably formulated in a unit dosage form with each dosage normally containing from about 50 μg to about 100 mg, more usually from about 1 mg to about 10 mg of the active ingredient. The term "unit dosage form" refers to physically discrete units suitable as unitary dosages for human subjects and other mammals, each unit containing a predetermined quantity of active material calculated to produce the desired therapeutic effect in association with a suitable pharmaceutical excipient.

For the purpose of parenteral administration, compositions containing a compound of the present invention preferably are combined with distilled water at an appropriate pH. Additional pharmaceutical methods may be employed to control the duration of action. Controlled release preparations may be achieved by the use of polymers to complex or absorb a compound of the present invention. The controlled delivery may be exercised by selecting appropriate macromolecules (for example, polyesters, polyamino acids, polyvinylpyrrolidone, ethylenevinyl acetate, methylcellulose, carboxymethylcellulose, and protamine sulfate) and the concentration of macromolecules as well as the methods of incorporation in order to control release.

Another possible method to control the duration of action by controlled release preparations is to incorporate a compound of the present invention into particles of a polymeric material such as polyesters, polyamino acids, hydrogels, poly (lactic acid) or ethylene vinylacetate copolymers. Alternatively, instead of incorporating a compound into these polymeric particles, it is possible to entrap a compound of the present invention in microcapsules prepared, for example, by coacervation techniques or by interfacial polymerization, for example, hydroxymethylcellulose or gelatin-microcapsules, respectively, or in colloidal drug delivery systems, for example, liposomes, albumin microspheres, microemulsions, nanoparticles, and nanocapsules, or in macroemulsions. Such teachings are disclosed in *Remington's Pharmaceutical Sciences* (1980).

The compounds of the present invention have insulinotropic activity. Thus, another aspect of the present invention provides a method for enhancing the expression of insulin comprising providing to a mammalian pancreatic B-type islet cell an effective amount of a compound of the present invention.

Similarly, the present invention provides a method for treating diabetes mellitus in a mammal, preferably a human, in need of such treatment comprising administering an effective amount of a compound or composition of the present invention, to such a mammal.

By way of illustration, the following examples are provided to help describe how to make and practice the various embodiments of the invention. These example are in no way meant to limit the scope of the invention.

EXAMPLE 1

Synthesis of (Arg26)GLP-1(8–37)OH

The polypeptide portion of Formula 1 wherein Xaa is Arg and $R^3$ is Gly-OH was prepared by solid phase synthesis on a Model 430A peptide synthesizer (PE-Applied Biosystems, Foster City, Calif.) using the Boc protecting strategy. The side chain protecting groups were: Asp (Chxl), Glu (OBzl), Ser (Bzl), Thr (Bzl), Lys (Cl-Z), His (BOM), Trp (CHO), Tyr (Br-Z), and Arg (Tos). All except for Asp (Chxl) (Peptides International) were obtained from PE-Applied Biosystems. Each residue was double coupled using either DCC initiated symmetric anhydride or HOBT activation. The 30 residue intermediate was left attached to the resin.

EXAMPLE 2

Synthesis of N-Imidazopropionyl (Arg26) GLP-1(8–37)OH

N-Cbz-Imidazol-4-yl propanoic acid (R. G. Jones, *J. Amer. Chem. Soc.*, 71, 383 (1949) was coupled to the (8–37)peptidyl resin described in Example 1 by placing 0.5 gm (1.8 mmol) of N-Cbz-imidazole-4-yl propanoic acid in each of two histidine cartridges and running the normal histidine double couple cycle on the Model 430A peptide synthesizer.

The modified peptityl resin prepared was treated with 20 ml of 20% piperidine in DMF (dimethyl formamide) at 4° C. for 1 hour to remove the Trp(CHO) protection. Approximately (2.6 gm) of the modified peptidyl resin was washed several times with $CH_2Cl_2$, transferred to a teflon reaction vessel and dried in vacuo. Two ml of m-cresol and a magnetic stir bar were added to the the vessel which was attached to an HF apparatus (Pennisula Laboraries, Inc.), cooled to −78° C., evacuated, and 20–25 ml HF was condensed into the vessel. The reaction mixture was stirred for 60 min in an ice bath and the HF was then removed by vacuum. The modified peptide residue (GLP-1 analog) was suspended in 200 ml ethyl ether and stirred briefly. The solid material was then filtered using a 60 ml glass fritted filter funnel. After washing the solids twice with ethyl ether, the GLP-1 analog was solubilized by washing the solids with 40 ml each of 50% aqueous acetic acid and 10% aqueous acetic acid. 100 ul of the combined aqueous filtrate was removed and prepared for standard HPLC analysis using the following conditions:

| Buffers: | A) 0.1% TFA |
| --- | --- |
|  | B) 0.1% TFA/50% $CH_3CN$ |
| Column: | Vydac C18 (0.46 × 15 cm) |
| Temperature: | 45° C. |
| Flow: | 1.0 ml/min. |
| Detector: | 214 nm |
| Gradient: | 0% B for 5 min., then 0 to 100% B over 60 min. |

The remaining aqueous filtrate (approximately 90 ml) was divided into two portions and each was loaded onto a 2.2× 25 cm Vydac C18 column and preparatively chromatographed (Pharmacia FPLC) at room temperature while monitoring at 214 nm. Fractions were collected every 5 min at a flow rate of 4 ml/min in a gradient beginning with 20% B (A and B were the same as above) and ending with 100% B over 790 min at room temperature.

UV absorbing fractions were analysed by HPLC and selected fractions (61–67) were combined and lyophilized to give 114 mg of the title compound. In like fashion, 175 mg was obtained from the second portion. The GLP-1 analog was characterized by fast atom bombardment (FAB), mass spectral analysis, and amino acid analysis. The molecular ion peak found (3369.2) agreed with the theoretical molecular weight (3368.7)+ 1. The amino acid ratios were consistant with the desired product:

| Amino acid | Theory | Found |
|---|---|---|
| Asp | 1 | 1.00 |
| Thr | 2 | 1.84 |
| Ser | 3 | 2.55 |
| Glu | 4 | 3.96 |
| Gly | 4 | 3.98 |
| Ala | 4 | 4.07 |
| Val | 2 | 1.95 |
| Ile | 1 | 0.9 |
| Leu | 2 | 1.94 |
| Tyr | 1 | 0.92 |
| Phe | 2 | 1.86 |
| Lys | 1 | 0.96 |
| Arg | 2 | 1.55 |

EXAMPLE 3

Synthesis of

N-Imidazopropionyl (Ara26 ($N^\epsilon$-Octanoyl (lysyl134)))GLP-1(8–37))OH

N-imidazolepropyl ((Arg26) GLP-1 (8–37)OH was acylated with N-succinimidyl-octanoate on the $N^\epsilon$-amine of Lys$^{34}$ in the following manner.

N-imidazopropionyl((Arg26)GLP-1(8–37))OH (70.5 mg; 0.021 mmol), as prepared in Examples 1 and 2, was dissolved in 25 ml of dimethylsulfoxide (DMSO). N-succinimidyl-octanoate (19.1 mg; 0.079 mmol) was then added and stirred into solution. A 10 fold molar excess of tetramethylguanidine (26.2 ml; 0.21 mmol) was added to ensure full deprotenation of the epsilon amino group. The reaction mixture was stirred at ambient temperature and monitored by HPLC. After 45 minutes the reaction was stopped with 100 ml of 0.1N HCl. Gelatinous particles were removed by passing the mixture through a glass-wool plug in a glass funnel.

Separation of the title product from starting materials was achieved on a C4 reverse-phase preparative HPLC column using the following conditions:

| Buffers: | A) 0.1% TFA, 5% acetonitrile |
| | B) 0.1% TFA, 95% acetonitrile |
| Column: | Vydac C4 (2.2 × 25 cm) |
| Temperature: | ambient |
| Flow: | 2.0 ml/min. |
| Detector: | 280 nm |
| Gradient: | 25–55% B over 300 min. |

The title product eluted at 44.6 to 46.7% acetonitrile as determined by analytical HPLC of individual fractions. The appropriate fractions were pooled, frozen and lyophilized. The reaction yielded 22.7 mg (32%) with an approximate purity of 87% by HPLC.

Additional purification was achieved using a second preparative HPLC step at pH=7.7 with the following conditions:

| Buffers: | A) 0.1M (NH$_4$)HCO$_3$, 10% acetonitrile |
| | B) 0.1M (NH$_4$)HCO$_3$, 50% acetonitrile |
| Column: | Vydac C18 (2.2 × 25 cm) |
| Temperature: | ambient |
| Flow: | 2.0 ml/min. |
| Detector: | 280 nm |
| Gradient: | 50–90% B over 300 min. |

The sample (22.7 mg) was dissolved in 20 ml of buffer A) and loaded onto the column. Separation of components was achieved using the above gradient. The title product eluted between 34.8 and 35.6% acetonitrile as determined by analytical HPLC. Appropriate fractions were pooled and lyophilized. The recovery was 10.46 mg (46.1%) of title product with an HPLC purity of approximately 99%. The overall recovery for both RP-HPLC steps on a weight basis was 14.8%.

EXAMPLE 4

Synthesis of
N-Imidazoacetyl(Ara26)GLP-1(8–37))OH

[N-(tert-Butoxycarbonyl)-imidazol-4-yl]acetic acid was prepared from 4-imidazoleacetic acid by protecting the the imidazole ring with with the tert-butoxycarbonyl in the following manner. Di-tert-butyl dicarbonate (1.1 equiv./equiv. of amine) was added to a mixture of the free amine, potassium carbonate (1.1 equiv.) and 50% aqueous dioxane, and the whole was stirred at room temperature for 4 hours. The resulting mixture was diluted with diethyl ether and the layers separated. The aqueous layer was acidified with 1.0N aqueous citric acid and extracted three times with methylene chloride. The extracts were dried (MgSO$_4$) and the solvent was removed in vacuo. The resulting oil was crystalized from an appropriate solvent.

The [N-(tert-Butoxycarbonyl)-imidazol-4-yl]acetic acid was then coupled to the (8–37)peptidyl resin described in Example 1 by placing approximately 0.5 gm (1.8 mmol) in each of two histidine cartridges and running the normal histidine double couple cycle on the Model 430A peptide synthesizer as described in Example 2.

The modified peptidyl resin was released from the resin and purified in substantial accordance with with Example 2. The UV absorbing fractions were analysed by HPLC and were then combined and lyophilized to give approximately 100 mg of the title compound. A sample was then characterized by fast atom bombardment (FAB) and mass spectral analysis. The molecular ion peak found agreed with the theoretical molecular weight.

EXAMPLE 5

Synthesis of
N-[Imidazole-α,α-dimethyl-acetyl]GLP-1 (8–37)OH

α,α-dimethyl-α-[N-(tertbutoxycarbonyl)imidazol-4-yl] acetic acid was prepared from N-trityl-α,α-dimethyl-4-imidazoleacetonitrile [J. I. DeGraw, et al., *JMC*, 20, 1671 (1977)] as follows.

N-trityl-α,α-dimethyl-4-imidazoleacetonitrile (3.97 g, 10.5 mmol) was added to a 5% conc. HCl/methanol solution (25 ml) and the whole refluxed for three hours before concentrating in vacuo. The remaining material was partitioned between 5N aq. HCl(25 ml) and ethyl acetate (50 ml). The aqueous layer was separated and refluxed for 24 hours. After concentrating in vacuo, the crude α,α,-dimethyl-4-imidazoleacetic acid was dissolved in water and concentrated again. The title compound (1.88 g, mp, 155° C.(dec)) was prepared from this crude acid by the general method described above.

The α,α-dimethyl-α-[N-(tertbutoxycarbonyl)imidazol-4-yl] acetic acid was then coupled to the (8–37) peptidyl resin in susbstantial accordance to the previous examples.

EXAMPLE 6

Synthesis of N-Imidazoacetyl-GLP-1(8–36)NH$_2$

GLP-1(8–36)NH$_2$ was produced by solid phase peptide chemistry on an Applied Biosystems (ABI) 460A peptide synthesizer using a MBHA resin (ABI, lot # A1A023, 0.77 mmol/g). All amino acids had their α-amino groups protected by the tertbutyloxycarbonyl (t-Boc) group. Those with reactive side chains had them protected as follows: Arg(Tos); Lys(Cl-Z); Trp(CHO); Glu(CHex); Tyr(Br-Z); Ser(Bzl); Asp(OBzl); Thr(Bzl).

The protected amino acids were activated in dichloromethane (DCM) with one half an equivalent of dicyclohexylcarbodiimide (DCC) per equivalent of amino acid to give the symmetric anhydride of the amino acid. However, arginine, glutamine, and gtycine residues were activated by forming the 1-hydroxybenzotriazole (HOBt) esters of these amino acids (1:1:1 equivalents of amino acid, HOBt, and DCC in dimtethylformamide (DMF)).

Residues were sequentially connected from the C-terminal towards the N-terminal end with a series of coupling and deprotection cycles. A coupling cycle consisted of the activated amino acid undergoing nucleophilic substitution by the free primary amine of the previously coupled amino acid. Deprotection was the removal of the N-terminal blocking group Boc with anhydrous trifluoroacetic acid (TFA). This generated a free amine group after neutralization with diisopropylethylamine (DIEA).

The synthesis scale was 0.5 mmol. The concentration of functional sites on the MBHA-resin was 0.77 mmol/g; 649 mg of resin was used. A two fold molar excess of the symmetric anhydride was used for all of the amino acids. The C-terminal Arginine was coupled to the MBHA-resin via standard protocols. All residues were double-coupled. That is each residue was coupled to the resin twice. The second coupling was performed without a Boc deprotection step prior to re-addition of the amino acid. This helped to completely react all of the free amine groups on the resin. The tryptophan residue was quadruple coupled.

The title compound was prepared using the peptidyl resin and the R group of Example 4 in substantial accordance with the previous examples. After the R group was added to the amino terminus and the formyl groups removed, the peptide was liberated from the resin by hydrolysis with liquid hydrofluoric acid (HF) at 0° C. for one hour using a Teflon reaction vessel. For every gram of peptidyl-resin, 1 ml of m-cresol scavenger was added and 10 ml of liquid HF used. The scavenger prevented the reattachment of side chain blocking groups (released as carbocations) to the peptide. After one hour, the HF was removed by vacuum leaving a slurry of peptide, resin, and m-cresol.

The peptide was then precipitated in the HF reaction vessel with ice cold diethyl ether. The precipitate was transferred to a 150 ml sintered glass funnel along with several ether rinses. The peptide/resin physical mixture was washed several times with cold ether to remove residual HF and m-cresol. The second step was to extract the peptide away from the resin using 10% acetic acid in water (v/v). Vacuum filtration into a clean round bottom flask yielded a crude peptide solution.

EXAMPLE 7

In vitro Receptor Binding Assay (cAMP Assay)

a) Rat, GLP-1 receptor, membrane preparation:

The published DNA sequence for the rat GLP-1 receptor (Thorens B., et. al. *Proc. Natl. Acad. Sci. U.S.A.* 89:8641–8645 (1992) and the dihydrofolate reductase resistance marker gene were used in conjunction with PCR techniques to construct an expression vector. The DXB-11 variant of the chinese hamster ovary (CHO) cell line was transformed with the vector, resulting in a recombinant CHO cell line that expressed the rat GLP-1 membrane receptor.

Cells were grown and harvested, and a membrane preparation was obtained by first washing the cells with PBS buffer, then twice washing with cold buffer (25 mM HEPES, 2 mM MgCl$_2$, 1 mM EDTA, 20 µg/ml Leupeptin, 1 mM PMSF, 2 µg/ml Aprotinin, 50 µg/ml Trypsin Inhibitor, pH 8.0) and resuspending in buffer. The cell suspension was lysed in a glass Teflon homogenizer, and the resulting sample was then centrifuged at 35,300×g for 30 minutes at 4° C. The supernatant was removed, and the pellet was resuspended in cold buffer and homogenized. Aliquots were stored at –80° C.

b) Cyclic AMP (cAMP) Assay:

A sample of the membrane preparation was preincubated with a test compound or a control compound in buffer (25 mM HEPES, 0.2% (w/v) BSA, pH 7.6) at 32° C. for 10 minutes. Reaction buffer (final concentration: 25 mM HEPES, 0.2% (w/v) BSA, 2.6 mM Mg, 0.8 mMATP, 0.1 mM GTP, 5 mM creatine phosphate, creatine kinase 50 U/ml, 0.2 mM IBMX, pH 7.6) was added and incubated for an additional 30 minutes. Incubations were stopped by adding 10 mM EDTA.

Production of cAMP was assayed using a fluorescent tracer-immuno assay method. In brief, after the incubation was stopped, fluorescent tracer (cAMP-b phycoerythrin conjugate) was added followed by the addition of affinity purified anti-cAMP rabbit antiserum. After incubation at room temperature for 45 minutes, anti-rabbit IgG coated assay beads were added and incubated for an additional 15 minutes. Plates were then evacuated and read on a Pandex PFCIA reader.

In this assay, a known insulinotropic agent such as GLP-1(7–37)OH showed decreasing fluorescent intensity due to increased cAMP concentration. Fluorescent intensity values were correlated to rate of cAMP production (pmol/min/mg). Conversely, agents having no insulinotropic action failed to stimulate production of cAMP and therefore showed no decrease in fluorescent intensity.

TABLE 1

| Compound | cAMP Assay % Relative Potency |
|---|---|
| GLP-1(7–37)OH | 100.0 ± 18 |
| Arg$^{26}$-GLP-1(7–37)OH | 140.8 ± 28.7 |
| N-imidazopropionyl-GLP-1(8–37)OH | 21.9 ± 7.8 |
| N-imidazopropionyl-Arg$^{26}$-GLP-1(8–37)OH | 89.0 ± 12.6 |
| N-imidazopropionyl-Arg$^{26}$-Lys$^{34}$-N$^\epsilon$-octanoyl-GLP-1(8–37)OH | 8.8 ± 1.4$^a$ |
| GLP-1(7–36)NH$_2$ | 88.4 ± 29.4 |

TABLE 1-continued cAMP Assay

| Compound | % Relative Potency |
|---|---|
| N-imidazoacetyl-GLP-1(8–36)NH$_2$ | 24.2 ± 9.8 |
| N-imidazoacetyl-Arg$^{26}$-GLP-1(8–37)OH | 95.0 ± 14.3 |
| α,α-imidazoacetyl-GLP-1(8–37)OH | 108.2 ± 22.4 |

[a]Acylated compounds generally gave artificially low potency values due to non specific binding.

EXAMPLE 8

Dog In vivo Assays a) Hyperglycemic Clamp Studies

Experiments were conducted in overnight-fasted, conscious, adult (1–2 years of age) male and female beagles weighing 8–15 kg. At least ten days prior to the study, animals were anesthetized with isoflurane, and a cut-down was made in the left or right inguinal region. Silastic catheters were inserted into the femoral artery and the proximal caudal femoral vein and secured with 4-0 silk suture. The free ends of the catheters were passed subcutaneously to the back using a trocar needle. The catheters were then filled with a glycerol/heparin solution (3:1, v/v; final heparin concentration of 250 KIU/ml), and the free ends were knotted and placed in a subcutaneous pocket to allow complete closure of the skin. Keflex® was administered both pre-operatively (20 mg/kg, IV and 20 mg/kg, I.M.) and post-operatively (250 mg, p.o. once daily for seven days) to prevent infections. Torbugesic (1.5 mg/kg, I.M.) was administered post-operatively to control pain.

Blood was drawn just prior to the study day to determine the health of the animal. Only animals with hematocrits above 38% and leukocyte counts below 16,000/mm$^3$ were used.

The afternoon before the experiment, the free ends of the catheters were exteriorized from the subcutaneous pocket through a small incision made under local anesthesia (2% lidocaine), and the dog was fitted with a tether system jacket and collar assembly.

The morning of the experiment, the contents of the catheters were aspirated, the catheters were flushed with saline, and extension lines (protected by a stainless steel tether) were attached to the catheters. On mornings of IV injection experiments, an over-the-needle, teflon catheter was inserted percutaneously into a cephalic vein in preparation for the administration of an IV bolus of test substance. The dog was placed in a metabolic cage, and the catheter extension lines and tether were attached to a swivel system to allow the dog to move freely about the cage. At this time (–60 minutes), an exogenous infusion of glucose (50% w/v in water) was begun through the chronic venous catheter. Glucose was infused in a descending stepwise fashion over the first six minutes of the study to rapidly raise the plasma glucose concentration to 150 mg/dl. Plasma glucose concentrations were determined every 2.5 to 7.5 minutes throughout the remainder of the study, and the glucose infusion rate was adjusted appropriately to maintain the plasma glucose concentration at 150 mg/dl.

Sixty minutes after the start of the glucose infusion (time 0), test substance was administered either intravenously (1.0, 2.9, 5.0 or 10.0 μg/kg; dose dissolved in 2 ml of saline containing 0.3% dog albumin, w/v) through the previously inserted teflon catheter or subcutaneously (10 μg/kg; 150 μM in phosphate buffered saline) in the dorsal aspect of the neck.

Arterial blood samples (3.5 ml) were taken at –30, –15, 0, 2.5, 5, 7.5, 10, 12.5, 15, 20, 30, 45, 60, 75, 90, 105 and 120 minutes during the IV studies and at –30, –15, 0, 3, 6, 9, 12, 15, 20, 30, 45, 60, 75, 90, 105 and 120 minutes during the SC studies. Samples were collected in vacuum blood collection tubes containing disodium EDTA and immediately placed on ice. To prevent proteolytic cleavage of GLP-1(7–37) in the plasma samples, 1.5 ml of the EDTA containing blood were transferred to a polypropylene tube containing 40 μl of aprotinin (10,000 KIU/ml) and mixed well. The samples were centrifuged, and the resulting plasma was transferred to polypropylene test tubes and stored on ice for the duration of the study.

At the conclusion of the experiment, the animal was anesthetized (isoflurane); the catheters were flushed with fresh saline and filled with the glycerol/heparin mixture; the free ends of the catheters were knotted and placed subcutaneously as described earlier; and antibiotic was administered (300 mg Keflex®, I.M.).

Plasma glucose concentrations were determined the day of the study using a glucose oxidase method in a Beckman glucose analyzer. Samples for other assays were stored at –70° C. until time for analysis. Insulin concentrations were determined using a commercial radioimmunoassay kit with porcine insulin as the standard. GLP-1(7–37) levels were determined using a double antibody immunoassay.

Change in insulin was calculated as the difference between the insulin concentration at time t and the time-averaged insulin concentration prior to injection of test substance (baseline). The area under the insulin change curve was calculated using the trapezoidal rule. Glucose infusion rate change was calculated as the difference between the glucose infusion rate during time interval x and the average glucose infusion rate during the 30 minutes prior to injection of test substance (baseline). The area under the glucose infusion rate change curve was calculated using the trapezoidal rule. Values are listed as the mean ± the standard error of the mean (SEM).

b) Euglycemic Clamp Studies

The euglycemic clamp studies were performed in a manner identical to the hyperglycemic SC studies with the exception that the plasma glucose concentration was maintained at or near normal basal levels throughout the study. To accomplish this, plasma glucose concentrations were determined every 2.5 to five minutes after injection of test substance. When the plasma glucose concentration decreased by greater than five mg/dl from pretreatment values, an exogenous infusion of glucose (aqueous solution of 50% glucose, w/v) was started through the indwelling venous catheter to try to maintain the plasma glucose concentration near baseline. Because the venous line and its extension were filled with heparinized saline and not glucose, there was a significant lag period between the time that the infusion was started and the time that glucose actually entered the dog. For this reason, glucose concentrations decreased below baseline for a short time after drug treatment. To obtain a more accurate estimate of the amount of glucose actually infused into the dogs, an estimate of the volume of dead space was obtained (930 μl), and the glucose infusion rates were corrected accordingly.

Change in insulin was calculated as the difference between the insulin concentration at time t and the time-averaged insulin concentration prior to injection of test substance (baseline). The area under the insulin change curve was calculated using the trapezoidal rule. Values are listed as the mean ± the standard error of the mean (SEM).

c) Oral Glucose Tolerance Tests

Oral glucose tolerance tests were performed in a group of four over-night fasted, male and female beagles weighing 12–14 kg. Preparation of the animals was identical to that described above. After placement in the metabolic cage, the animals were allowed a twenty minute rest period before the experiment was begun. At the end of this acclimation period, a zero sample was drawn; a thirty inch, 24 Fr. rubber colon tube was slipped through the esophagus into the stomach of the animal; a glucose bolus (1.5 g/kg; 50% glucose w/v in water) followed by a 20 ml bolus of distilled water was injected through the tube into the stomach; and the clock was started. Two minutes later a subcutaneous bolus of test substance (3 nmol/kg or approximately 10 µg/kg; 150 µM in phosphate buffered saline) was injected in the dorsal aspect of the neck.

In addition to the zero sample, arterial blood samples (3.5 ml) were taken at 5, 10, 15, 20, 30, 40, 50, 60, 75, 90, 105, 120, 135, 150, 165, 180, 195, 210, 225 and 240 minutes after administration of glucose. Samples were collected in vacuum blood collection tubes containing disodium EDTA and handled as described above.

At the conclusion of the experiment, the animal was anesthetized (isoflurane); the catheters were flushed with fresh saline and filled with the glycerol/heparin mixture; the free end of the catheters were knotted and placed subcutaneously as described earlier; and antibiotic was administered (300 mg Keflex®, I.M.).

Each of the four dogs was studied on three separate occasions: once with subcutaneous administration of phosphate buffered saline, once with GLP-1(7–37)OH, and once with N-Imidazopropionyl (Arg26(N$^\epsilon$-Octanoyl(lysyl34)))GLP-1(8–37))OH. Experiments in animals being restudied were carried out a minimum of one week apart. The leukocyte count and the hematocrit were determined the day before all experiments.

The insulin area under the curve above baseline (zero time insulin value) was calculated using the trapezoidal rule. The glucose area under the curve above baseline (zero time glucose value) was calculated using the trapezoidal rule. Values are listed as the mean ± the standard error of the mean (SEM).

TABLE 2

| | Dog I.V. Hyperglycemic (150 mg/dl) Clamp Test | | | | | |
|---|---|---|---|---|---|---|
| Compound | Dose (µg/kg) | n | Duration of Insulin Effect (min)$^a$ | Max Insulin Change (ng/ml)$^b$ | Insulin Change AUC (ng/ml · min; 0–60 min)$^c$ | GIR Change AUC (mg/kg; 0–60 min)$^d$ |
| Vehicle | 0 | 7 | not active | 0.8 ± 0.2 | 7 ± 14 | 238 ± 46 |
| GLP-1(7–36)NH$_2$ | 1.0 | 7 | 2.5 | 3.4 ± 0.6 | 32 ± 8 | 414 ± 73 |
| N-imidazopropionyl-GLP-1(8–37)OH | 1.0 | 3 | 7.5 | 3.1 ± 0.8 | 52 ± 18 | 399 ± 63 |
| N-imidazopropionyl-Arg$^{26}$-GLP-1(8–37)OH | 1.0 | 3 | 12.5 | 2.6 ± 0.6 | 38 ± 16 | 419 ± 122 |
| Lys$^{34}$-N$^\epsilon$-octanoyl-GLP-1(7–37)OH | 1.0 | 3 | 15 | 3.8 ± 1.0 | 50 ± 2 | 463 ± 12 |
| N-imidazopropionyl-Arg$^{26}$-Lys$^{34}$-N$^\epsilon$-octanoyl-GLP-1(8–37)OH | 1.0 | 4 | 42.5 | 2.3 ± 0.8 | 90 ± 40 | 350 ± 93 |
| | 5.0 | 3 | 72.5 | 3.8 ± 0.2 | 132 ± 7 | 568 ± 126 |
| N-imidazopropionyl-Arg$^{26}$-Lys$^{34}$-N$^\epsilon$-decanoyl-GLP-1(8–37)OH | 5.0 | 2 | not active | 0.9 ± 0.9 | 14 ± 10 | 236 ± 58 |

$^a$Duration of Insulin Effect: The time over which the average change in insulin was consistently ≧0.5 ng/ml.
$^b$Max Insulin Change: Maximum increase in insulin over baseline observed during the 120 minute test period.
$^c$Insulin Change AUC: Area under the insulin change curve; represents the total insulinotropic effect of the peptide.
$^d$GIR Change AUC: Area under the glucose infusion rate change curve; represents the overall metabolic effect of the peptide.

TABLE 3

| | Dog S.C. Hyperglycemic (150 mg/dl) Clamp Test | | | | | |
|---|---|---|---|---|---|---|
| Compound | Dose (µg/kg) | n | Duration of Insulin Effect (min)$^a$ | Max Insulin Change (ng/ml)$^b$ | Insulin Change AUC (ng/ml · min; 0–120 min)$^c$ | GIR Change AUC (mg/kg; 0–120 min)$^d$ |
| Vehicle | 0 | 5 | not active | 0.4 ± 0.2 | 11 ± 20 | 528 ± 224 |
| GLP-1(7–37)OH | 10 | 5 | 27 | 1.6 ± 0.8 | 64 ± 33 | 696 ± 145 |
| N-imidazopropionyl-Arg$^{26}$-GLP-1(8–37)OH | 10 | 4 | 42 | 3.6 ± 1.0 | 97 ± 39 | 811 ± 216 |
| Lys$^{34}$-N$^\epsilon$-octanoyl-GLP-1(7–37)OH | 10 | 5 | not active | 0.6 ± 0.3 | 29 ± 8 | 532 ± 112 |
| Arg$^{26}$-Lys$^{34}$-N$^\epsilon$-octanoyl- | 10 | 4 | not active | 0.6 ± 0.4 | 11 ± 26 | 659 ± 182 |

TABLE 3-continued

| | | | Dog S.C. Hyperglycemic (150 mg/dl) Clamp Test | | | |
|---|---|---|---|---|---|---|
| Compound | Dose (μg/kg) | n | Duration of Insulin Effect (min)[a] | Max Insulin Change (ng/ml)[b] | Insulin Change AUC (ng/ml · min; 0–120 min)[c] | GIR Change AUC (mg/kg; 0–120 min)[d] |
| GLP-1(8–37)OH N-imidazopropionyl-Arg[26]-Lys[34]-N[ε]-octanoyl-GLP-1(8–37)OH | 10 | 5 | >90 | 2.0 ± 0.4 | 113 ± 24 | 926 ± 268 |

[a]Duration of Insulin Effect: The time over which the average change in insulin was consistently >0.5 ng/ml.
[b]Max Insulin Change: Maximum increase in insulin over baseline observed during the 120 minute test period.
[c]Insulin Change AUC: Area under the insulin change curve; represents the total insulinotropic effect of the peptide.
[d]GIR Change AUC: Area under the glucose infusion rate change curve; represents the overall metabolic effect of the peptide.

EXAMPLE 9

Rat In Vivo Assays a) Glucose Tolerance Tests

Experiments were conducted in overnight-fasted, conscious, male Sprague Dawley (Charles River) or Zucker Diabetic Fatty (Genetic Models, Inc.) rats weighing approximately 250 (Sprague Dawley rats) or 300 (Zucker Diabetic Fatty rats) grams. Four to five days prior the study, rats were anesthetized with isoflurane, and a polyethylene (PE50) catheter was inserted into the right jugular vein. The catheter was secured with a wound clip, filled with saline containing heparin (2% sodium heparin), and closed with a small stainless steel plug.

After a sixteen-hour fast, twelve chronically cannulated rats were separated into four groups of three rats per group. 0.4 ml of blood was taken from the tail vein, collected into a microtainer tube containing lithium heparin, and immediately placed on ice (zero minute sample). A glucose bolus (1.0 g/kg; 50% glucose (w/v) in water) was administered via the indwelling jugular cannula, and the cannula was rinsed with 200 μl of saline. Twenty seconds later a bolus of test substance [100 μl/100 g body weight of either vehicle (saline containing 0.3% (w/v) bovine serum albumin) or vehicle containing analog] was administered through the jugular cannula, and the cannula was rinsed as before. Rats were bled from the tail again at 2, 5, 10, 20 and 30 minutes after the administration of the glucose bolus, and the samples were treated as described above. At the end of the experiment, blood samples were centrifuged, and the plasma was collected.

Plasma glucose concentrations were determined the day of the experiment using a coupled hexokinase procedure in a clinical chemistry analyzer. Plasma for insulin determinations were diluted with zero calibrator and frozen at −20° C. until time for analysis. Insulin concentrations were determined using a commercial radioimmunoassay kit with rat insulin as the standard.

Insulin change (the change in insulin from the baseline value) was calculated as the difference between the insulin concentration at time t and the insulin concentration at zero time. The area under the insulin change curve was calculated using the trapezoidal rule. Plasma glucose change (the increase in plasma glucose above the baseline value) was calculated as the difference between the plasma glucose concentration at time t and the plasma glucose concentration at zero time. The area under the plasma glucose change curve was calculated using the trapezoidal rule. Values are listed as the mean ± the standard error of the mean (SEM).

b) Hyperglycemic Clamp Studies

Experiments were conducted in chronically catheterized, normal, male Sprague Dawley rats weighing about 350 grams. At least a week prior to studies, surgery was performed on the rats under isoflurane anesthesia. Two catheters were implanted into the jugular vein for infusions of glucose and peptide and one catheter into the carotid artery for blood sampling. The catheters were exteriorized through the skin at the vertex of the head, filled with glycerol/heparin solution (3:1,v/v) and closed off with a one centimeter stainless steel plug. Animals were housed individually in wire mesh cages and allowed free access to standard rat chow diet and water.

Catheterized rats were fasted overnight prior to studies. On the morning of the experiment, rats were weighed and sampling tubings connected to their indwelling catheters. The tubings were enclosed in a light weight stainless steel spring for protection. During the study, rats were kept unrestrained in a plastic shoe box cage (12"×10"×12") with about one inch of bedding. After 15 minutes of acclimation, a basal sample was taken for measurement of insulin and glucose levels. At time −60 minutes, rats were given a bolus of 20% dextrose to raise plasma glucose to 150 mg/dl. The plasma glucose concentration was maintained at this level for the duration of the study by measuring the plasma glucose concentration every five minutes and adjusting the calibrated variable infusion pump accordingly. Blood samples were collected at −15 and 0 minutes for baseline measurements. Immediately after taking the zero minute sample, peptide (130–155 μM stock concentration, diluted in phosphate buffered saline) was injected via the jugular vein catheter and flushed with saline. Blood samples were taken for glucose and insulin determinations at 2, 4, 6, 8, 10, 12, 15, 20, 25, 30, 40, 50, 60, 70, 80, and 90 minutes. All blood samples were collected into syringes coated with sodium heparin, transferred into micro centrifuge tubes and placed on ice. Blood samples were then centrifuged in a micro centrifuge to separate the plasma component.

Plasma glucose levels were determined on the day of the study by the glucose oxidase method using the Beckman Glucose Analyzer 2, while the insulin concentrations were measured by a commercial kit (Diagnostic Products Corporation) with rat insulin standard.

Insulin change (the change in insulin from the baseline value) was calculated as the difference between the insulin concentration at time t and the average insulin concentration prior to injection of test substance. The area under the insulin change curve was calculated using the trapezoidal rule. Glucose infusion rate change (the percent change in the glucose infusion rate from the baseline value) was calculated as the difference between the glucose infusion rate value at time t and the average glucose infusion rate prior to injection of test substance, divided by the average glucose infusion rate prior to injection of test substance, times 100. The area under the glucose infusion rate change curve was calculated on the absolute glucose infusion rate change values (calculated as the difference between the glucose infusion rate value at time t and the glucose infusion rate prior to injection of test substance) using the trapezoidal rule. Values are listed as the mean ± the standard error of the mean (SEM).

TABLE 4

Rat IV Glucose (1 g/kg) Tolerance Test

| Compound | Dose mg/kg | n | Insulin Change AUC ng/ml · min; 0–15 min[a] | Max Insulin Change (ng/ml)[b] | Insulin Change at 10 min (ng/ml)[c] |
|---|---|---|---|---|---|
| Vehicle | 0 | 196 | 33 ± 1 | 2.9 ± 0.1 | 2.2 ± 0.1 |
| GLP-1(7–36)NH$_2$ | 0.2 | 5 | 34 ± 4 | 4.0 ± 0.8 | 1.8 ± 0.5 |
|  | 0.3 | 4 | 50 ± 13 | 6.1 ± 0.7 | 2.2 ± 1.2 |
|  | 0.4 | 5 | 73 ± 14 | 7.7 ± 1.0 | 3.8 ± 1.0 |
|  | 0.6 | 6 | 67 ± 11 | 7.7 ± 1.2 | 3.4 ± 0.9 |
|  | 0.8 | 3 | 97 ± 25 | 11.3 ± 2.8 | 4.1 ± 1.8 |
|  | 1.0 | 8 | 89 ± 16 | 11.4 ± 2.3 | 3.9 ± 0.7 |
|  | 2.0 | 5 | 106 ± 11 | 11.7 ± 1.3 | 4.9 ± 0.7 |
| GLP-1(7–37)OH | 0.6 | 3 | 79 ± 8 | 7.8 ± 1.1 | 5.4 ± 1.2 |
|  | 0.92 | 2 | 75 ± 12 | 8.4 ± 0.2 | 3.5 ± 1.2 |
|  | 1.2 | 3 | 77 ± 17 | 8.4 ± 1.6 | 4.2 ± 1.3 |
| N-imidazoacetyl-GLP-1(8–36)NH$_2$ | 0.05 | 3 | 49 ± 6 | 4.9 ± 0.9 | 2.5 ± 0.2 |
|  | 0.15 | 3 | 55 ± 8 | 5.9 ± 1.4 | 2.8 ± 0.1 |
|  | 0.3 | 3 | 98 ± 29 | 10.5 ± 2.3 | 5.5 ± 1.4 |
|  | 0.6 | 3 | 105 ± 4 | 13.0 ± 0.4 | 4.8 ± 0.1 |
|  | 0.92 | 3 | 95 ± 11 | 12.0 ± 1.2 | 4.0 ± 0.5 |
|  | 1.2 | 2 | 117 ± 6 | 13.7 ± 0.5 | 6.0 ± 0.4 |
| N-imidazoacetyl-Arg$^{26}$-GLP-1(8–37)OH | 1.2 | 2 | 85 ± 13 | 9.8 ± 2.5 | 3.6 ± 0.5 |
|  | 2.4 | 3 | 170 ± 16 | 16.5 ± 3.9 | 9.8 ± 2.5 |
| N-imidazopropionyl-GLP-1(8–37)OH | 0.1 | 3 | 70 ± 4 | 7.8 ± 0.3 | 3.2 ± 0.5 |
|  | 0.2 | 9 | 92 ± 6 | 10.2 ± 0.6 | 5.0 ± 0.6 |
|  | 0.4 | 6 | 74 ± 12 | 7.7 ± 1.6 | 4.8 ± 0.7 |
|  | 0.8 | 6 | 121 ± 16 | 13.3 ± 1.8 | 7.5 ± 1.1 |
|  | 1.0 | 4 | 98 ± 11 | 12.4 ± 1.6 | 5.4 ± 0.4 |
|  | 2.0 | 4 | 127 ± 24 | 16.1 ± 3.0 | 5.9 ± 1.1 |
| N-imidazopropionyl-Arg$^{26}$-GLP-1(8–37)OH | 0.6 | 2 | 114 ± 13 | 11.8 ± 2.1 | 7.7 ± 0.8 |
|  | 0.92 | 3 | 85 ± 7 | 9.2 ± 1.8 | 5.5 ± 0.9 |
|  | 1.2 | 6 | 127 ± 13 | 12.9 ± 1.8 | 8.2 ± 1.1 |
| Lys$^{34}$-N$^\epsilon$-octanoyl-GLP-1(7–37)OH | 0.6 | 3 | 33 ± 8 | 5.0 ± 2.3 | 1.3 ± 0.2 |
|  | 1.2 | 3 | 136 ± 30 | 13.1 ± 2.0 | 10.0 ± 2.8 |
| N-imidazopropionyl-Arg$^{26}$-Lys$^{34}$-N$^\epsilon$-octanoyl-GLP-1(8–37)OH | 1.2 | 6 | 100 ± 18 | 8.5 ± 1.7 | 8.3 ± 1.5 |
|  | 1.6 | 3 | 60 ± 11 | 5.9 ± 1.6 | 4.3 ± 0.7 |
|  | 2.4 | 3 | 128 ± 22 | 12.9 ± 2.5 | 10.1 ± 1.6 |

[a]Insulin Change AUC: The area under the insulin change curve; a representation of the total insulinotropic activity of the peptide.
[b]Max Insulin Change: The maximum increase in insulin over baseline (usually five minutes post-injection).
[c]Insulin Change at 10 min: The change in insulin from baseline measured 10 minutes post-injection. In active analogs, the closer this value is to the max insulin change (as a percent), the longer the time action of the analog.

TABLE 5

| | Rat I.V. Hyperglycemic (150 mg/dl) Clamp Test | | | | | |
|---|---|---|---|---|---|---|
| Compound | Dose (µg/kg) | n | Duration of Insulin Effect (min)[a] | Max Insulin Change (ng/ml)[b] | Insulin Change AUC[c] (ng/ml · min; 0–15 min)[c] | GIR Change AUC (mg/kg; 0–30 min)[d] |
| Vehicle | 0 | 4 | not active | 0.1 ± 0.1 | 0.5 ± 1.7 | 39 ± 10 |
| GLP-1(7–37)OH | 0.05 | 4 | 6 | 1.6 ± 0.3 | 3.0 ± 1.6 | 48 ± 22 |
| | 0.1 | 4 | 6 | 3.6 ± 1.2 | 7.3 ± 2.8 | 150 ± 25 |
| | 0.2 | 3 | 6 | 2.8 ± 0.1 | 5.8 ± 0.9 | 154 ± 10 |
| | 0.6 | 4 | 6 | 4.9 ± 1.3 | 14.9 ± 2.9 | 151 ± 46 |
| | 1.0 | 5 | 6 | 7.7 ± 0.8 | 16.7 ± 4.0 | 131 ± 29 |
| | 2.0 | 4 | 6 | 3.6 ± 0.9 | 11.5 ± 1.0 | 152 ± 36 |
| | 4.0 | 4 | 40 | 2.0 ± 0.4 | 10.4 ± 5.0 | 139 ± 27 |
| N-imidazopropionyl-Arg$^{26}$-GLP-1(8–37)OH | 1.0 | 5 | 15 | 6.6 ± 2.2 | 25.6 ± 3.6 | 324 ± 45 |
| Lys$^{34}$-N$^{\epsilon}$-octanoyl-GLP-1(7–37)OH | 1.0 | 4 | 4 | 2.4 ± 0.8 | 13.2 ± 2.5 | 132 ± 38 |
| N-imidazopropionyl-Lys$^{34}$-N$^{\epsilon}$-octanoyl-GLP-1(8–37)OH | 1.0 | 5 | 5 | 1.0 ± 0.2 | 7.6 ± 2.5 | 183 ± 38 |
| Arg$^{26}$-Lys$^{34}$-N$^{\epsilon}$-octanoyl-GLP-1(7–37)OH | 0.05 | 4 | 30 | 0.7 ± 0.2 | 6.3 ± 1.4 | 75 ± 32 |
| | 1.0 | 4 | 20 | 5.2 ± 1.8 | 35.5 ± 10.9 | 294 ± 25 |
| | 2.0 | 5 | 10 | 3.8 ± 0.9 | 32.5 ± 10.4 | 245 ± 58 |
| | 4.0 | 5 | 20 | 4.7 ± 0.8 | 35.7 ± 4.8 | 274 ± 71 |
| N-imidazopropionyl-Arg$^{26}$-Lys$^{34}$-N$^{\epsilon}$-octanoyl-GLP-1(8–37)OH | 0.05 | 4 | 8 | 0.5 ± 0.2 | 3.3 ± 1.4 | 124 ± 34 |
| | 1.0 | 5 | 30 | 4.2 ± 1.3 | 26.5 ± 7.8 | 218 ± 41 |
| | 2.0 | 4 | 60 | 5.2 ± 2.1 | 45.4 ± 15.5 | 351 ± 66 |
| | 4.0 | 4 | 40 | ~6.0 ± 3.0 | 45.5 ± 13.8 | 380 ± 40 |
| N-imidazopropionyl-Arg$^{26}$-1-Lys$^{34}$-N$^{\epsilon}$-decanoyl-GLP-1(8–37)OH | 1.0 | 4 | 15 | 0.8 ± 0.1 | 4.5 ± 2.0 | 83 ± 17 |

[a]Duration of Insulin Effect: Time over which the average change in insulin was >0 ng/ml.
[b]Max Insulin Change: Maximum increase in insulin over baseline during the 90 minute test period.
[c]Insulin Change AUC: Area under the insulin change curve; represents the total insulinotropic effect of the peptide.
[d]GIR Change AUC: Area under the glucose infusion rate change (in mg/kg/min) curve; represents the overall metabolic effect of the peptide

We claim:

1. A compound of the formula:

(SEQ. ID. NO:1) (Formula 1)

R$^1$—Ala—Glu—Gly—Thr—Phe—Thr—Ser—Asp—Val—

Ser—Ser—Tyr—Leu—Glu—Gly—Gln—Ala—Ala—Xaa—

Glu—Phe—Ile—Ala—Trp—Leu—Val—Lys—Gly—Arg—R$^3$
                                          |
                                          R$^2$ wherein R$^1$ is selected from the group consisting of 4-imidazopropionyl, 4-imidazoacetyl, or 4-imidazo-α,αdimethylacetyl;

R$^2$ is selected from the group consisting of $C_6$–$C_{10}$ unbranched acyl, or is absent;

R$^3$ is selected from the group consisting of Gly-OH or NH$_2$; and,

Xaa is Lys or Arg.

2. The compound of claim 1 wherein R$^1$ is 4-imidazopropionyl, R$^2$ is $C_8$ unbranched acyl, R$_3$ is Gly-OH, and Xaa is Arg.

3. The compound of claim 2 wherein R$^2$ is absent.

4. The compound of claim 1 wherein R$^1$ is 4-imidazoacetyl and R$^2$ is $C_8$ unbranched acyl.

5. The compound of claim 4 wherein R$^2$ is absent.

6. The compound of claim 1 wherein R$^1$ is 4-imidazo-α,αdimethyl-acetyl and R$^2$ is $C_8$ unbranched acyl.

7. The compound of claim 6 wherein R$^2$ is absent.

8. A pharmaceutical composition comprising the compound of claim 1 in combination with a pharmaceutically acceptable carrier, diluent, or excipient.

9. A pharmaceutical composition comprising the compound of claim 2 in combination with a pharmaceutically acceptable carrier, diluent, or excipient.

10. A pharmaceutical composition comprising the compound of claim 3 in combination with a pharmaceutically acceptable carrier, diluent, or excipient.

11. A pharmaceutical composition comprising the compound of claim 4 in combination with a pharmaceutically acceptable carrier, diluent, or excipient.

12. A pharmaceutical composition comprising the compound of claim 5 in combination with a pharmaceutically acceptable carrier, diluent, or excipient.

13. A pharmaceutical composition comprising the compound of claim 6 in combination with a pharmaceutically acceptable carrier, diluent, or excipient.

14. A pharmaceutical composition comprising the compound of claim 7 in combination with a pharmaceutically acceptable carrier, diluent, or excipient.

15. A method for treating non-insulin dependent diabetes mellitus in a mammal in need of such treatment comprising administering an effective amount of the compound of claim 1 to said mammal.

16. A method for treating non-insulin dependent diabetes mellitus in a mammal in need of such treatment comprising administering an effective amount of the compound of claim 2 to said mammal.

17. A method for treating non-insulin dependent diabetes mellitus in a mammal in need of such treatment comprising administering an effective amount of the compound of claim 3 to said mammal.

18. A method for treating non-insulin dependent diabetes mellitus in a mammal in need of such treatment comprising administering an effective amount of the compound of claim 4 to said mammal.

19. A method for treating non-insulin dependent diabetes mellitus in a mammal in need of such treatment comprising administering an effective amount of the compound of claim 5 to said mammal.

20. A method for treating non-insulin dependent diabetes mellitus in a mammal in need of such treatment comprising administering an effective amount of the compound of claim 6 to said mammal.

21. A method for treating non-insulin dependent diabetes mellitus in a mammal in need of such treatment comprising administering an effective amount of the compound of claim 7 to said mammal.

22. The method of claim 15 wherein the mammal is a human and the compound is administered sub-cutaneously.

23. The method of claim 16 wherein the mammal is a human and the compound is administered sub-cutaneously.

24. The method of claim 17 wherein the mammal ms a human and the compound is administered sub-cutaneously.

25. The method of claim 18 wherein the mammal ms a human and the compound is administered sub-cutaneously.

26. The method of claim 19 wherein the mammal ms a human and the compound is administered sub-cutaneously.

27. The method of claim 20 wherein the mammal is a human and the compound is administered sub-cutaneously.

28. The method of claim 21 wherein the mammal ms a human and the compound is administered sub-cutaneously.

* * * * *